United States Patent
Fujii et al.

(10) Patent No.: US 11,525,998 B2
(45) Date of Patent: Dec. 13, 2022

(54) ENDOSCOPE OBJECTIVE LENS UNIT AND ENDOSCOPE

(71) Applicant: HOYA CORPORATION, Tokyo (JP)

(72) Inventors: Hiroaki Fujii, Tokyo (JP); Sachiko Nasu, Tokyo (JP)

(73) Assignee: HOYA CORPORATION, Tokyo (JP)

(*) Notice: Subject to any disclaimer, the term of this patent is extended or adjusted under 35 U.S.C. 154(b) by 400 days.

(21) Appl. No.: 16/645,973

(22) PCT Filed: Sep. 7, 2018

(86) PCT No.: PCT/JP2018/033289
§ 371 (c)(1),
(2) Date: Mar. 10, 2020

(87) PCT Pub. No.: WO2019/054308
PCT Pub. Date: Mar. 21, 2019

(65) Prior Publication Data
US 2020/0201021 A1 Jun. 25, 2020

(30) Foreign Application Priority Data
Sep. 12, 2017 (JP) .............................. JP2017-174964

(51) Int. Cl.
*G02B 21/02* (2006.01)
*G02B 23/24* (2006.01)
(Continued)

(52) U.S. Cl.
CPC ........ *G02B 23/243* (2013.01); *A61B 1/00096* (2013.01); *A61B 1/00186* (2013.01); *A61B 1/05* (2013.01); *G02B 13/04* (2013.01)

(58) Field of Classification Search
CPC .. G02B 23/243; G02B 13/04; A61B 1/00096; A61B 1/00186; A61B 1/05
(Continued)

(56) References Cited

U.S. PATENT DOCUMENTS 6,956,703 B2  10/2005  Saito
8,094,382 B2   1/2012  Agatsuma
(Continued)

FOREIGN PATENT DOCUMENTS

JP  7-253536 A   10/1995
JP  2006-64904 A  3/2006
(Continued)

OTHER PUBLICATIONS

U.S. Appl. No. 16/646,355 to Hiroaki Fujii et al., filed Mar. 11, 2020.
(Continued)

*Primary Examiner* — William Choi
(74) *Attorney, Agent, or Firm* — Greenblum & Bernstein, P.L.C.

(57) ABSTRACT

The objective lens unit includes, a front lens group having a negative refractive power, a diaphragm, and a rear lens group having a positive refractive power, in order from an object side. The front lens group includes a negative lens having a concave surface facing an image surface side, and a positive lens having a convex surface facing the object side, and the rear lens group includes a positive lens having a convex surface facing the image surface side and a cemented lens in which a positive lens and a negative lens are cemented. The endoscope objective lens unit satisfies $-1.6 < f_F/f_R < -1.2$ and $-1.0 < SF_5 < -0.5$. $f_F$ and $f_R$ are the focal lengths of the front lens group and the rear lens group, $SF_5$ is $(R_{51}+R_{52})/(R_{51}-R_{52})$, and $R_{51}$ and $R_{52}$ are respectively the curvature radiuses of surfaces.

5 Claims, 7 Drawing Sheets

(51) Int. Cl.
*A61B 1/00* (2006.01)
*A61B 1/05* (2006.01)
*G02B 13/04* (2006.01)

(58) Field of Classification Search
USPC .............. 359/644, 646, 650, 651, 659, 661
See application file for complete search history.

(56) References Cited

U.S. PATENT DOCUMENTS

| | | |
|---|---|---|
| 8,164,839 B2 | 4/2012 | Nasu |
| 8,498,057 B2 | 7/2013 | Nakamura |
| 8,767,320 B2 | 7/2014 | Fujii |
| 9,140,888 B2 | 9/2015 | Fujii |
| 10,036,883 B2 | 7/2018 | Fujii |
| 10,082,648 B2 | 9/2018 | Usui et al. |
| 10,088,666 B2 | 10/2018 | Nasu et al. |
| 10,209,506 B2 | 2/2019 | Fujii et al. |
| 2004/0002400 A1 | 12/2004 | Saito |
| 2004/0240081 A1 | 12/2004 | Saito |
| 2006/0056067 A1 | 3/2006 | Yanai et al. |
| 2008/0198478 A1 | 8/2008 | Yanai et al. |
| 2011/0002052 A1 | 1/2011 | Nasu |
| 2012/0127598 A1* | 5/2012 | Katahira ............ G02B 23/2423 359/781 |
| 2014/0268369 A1 | 9/2014 | Chen et al. |
| 2017/0023778 A1* | 1/2017 | Inoue ................... G02B 23/243 |
| 2017/0303774 A1 | 10/2017 | Nasu |
| 2018/0149838 A1 | 5/2018 | Takakubo et al. |
| 2019/0053695 A1 | 2/2019 | Fujii et al. |

FOREIGN PATENT DOCUMENTS

| | | |
|---|---|---|
| JP | 4245985 B2 | 4/2009 |
| JP | 2011-13647 A | 1/2011 |

OTHER PUBLICATIONS

International Search Report issued in International Patent Application No. PCT/JP2018/033289, dated Dec. 11, 2018, along with an English translation thereof.

* cited by examiner

ENDOSCOPE OBJECTIVE LENS UNIT AND ENDOSCOPE

TECHNICAL FIELD

The present invention relates to an endoscope objective lens unit and an endoscope.

BACKGROUND ART

Today, endoscopes are used to examine biological tissue inside a human body. An endoscope includes an image sensor that captures an image of a biological tissue illuminated with illumination light and an objective lens unit attached to the image sensor at a distal end portion that is inserted into a human body. Since the objective lens unit needs to be very small and have high optical performance in order to reduce the size of the distal end portion, it is often configured with a small number of lenses.

For example, there is a known endoscope objective lens that includes a front lens group, a diaphragm, and a rear lens group in order from an object side, in which the front lens group is composed of a negative lens and a positive lens having a surface with a small curvature radius on the object side in order from the object side, and the rear lens group is composed of a positive lens having a surface with a small curvature radius on the image side and a cemented lens in which a positive lens and a negative lens are cemented, and there is a predetermined relationship between a focal length f of the entire system and a focal length $f_3$ of the positive lens in the rear lens group (Patent Document 1).

According to the above endoscope objective lens, it is said that a lens having a wide angle, a small outer diameter, and a low maximum light beam height of the first lens can be provided.

CITATION LIST

Patent Literature

Patent Literature 1: JP 4245985 B2

SUMMARY OF INVENTION

Technical Problem

In an endoscope, generally, a small charge-coupled device (CCD) image sensor is often used as an image sensor, and is designed so that an incident angle of incident light entering onto the image sensor become small. In addition, this image sensor is designed so that the back focus becomes long in order to transmit incident light before light reception through a filter, a prism, or the like.

In recent years, image sensors that can receive light even when the incident angle of incident light is large, such as complementary metal oxide (CMOS) image sensors, have been developed. However, an endoscope objective lens with a large angle of view that can efficiently use an image sensor that can capture incident light with a large incident angle is not known.

Therefore, an object of the present invention is to provide an endoscope objective lens capable of increasing the angle of view while maintaining good optical performance, and an endoscope including the endoscope objective lens.

Solution to Problem

Figure 2:
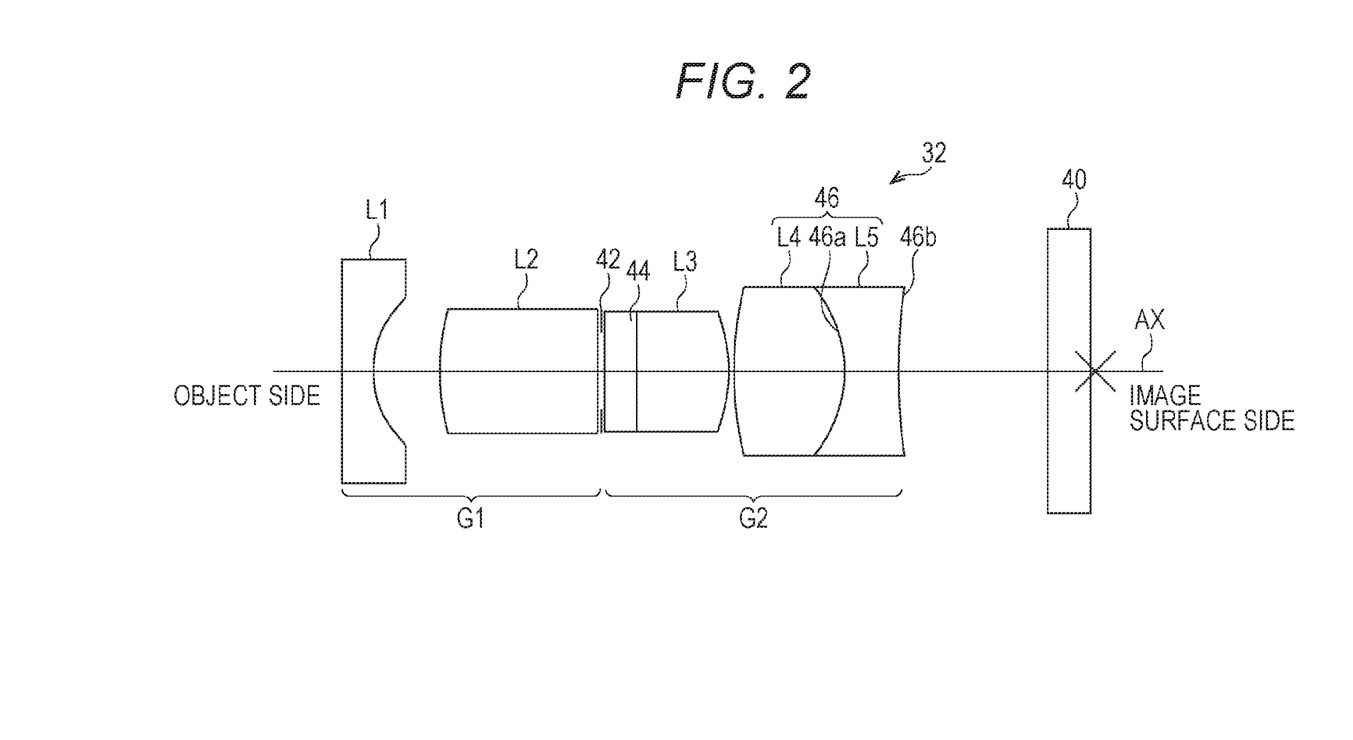
FIG. 2 is a diagram illustrating an example of a configuration of the endoscope objective lens unit according to the present embodiment.
Figure 3:
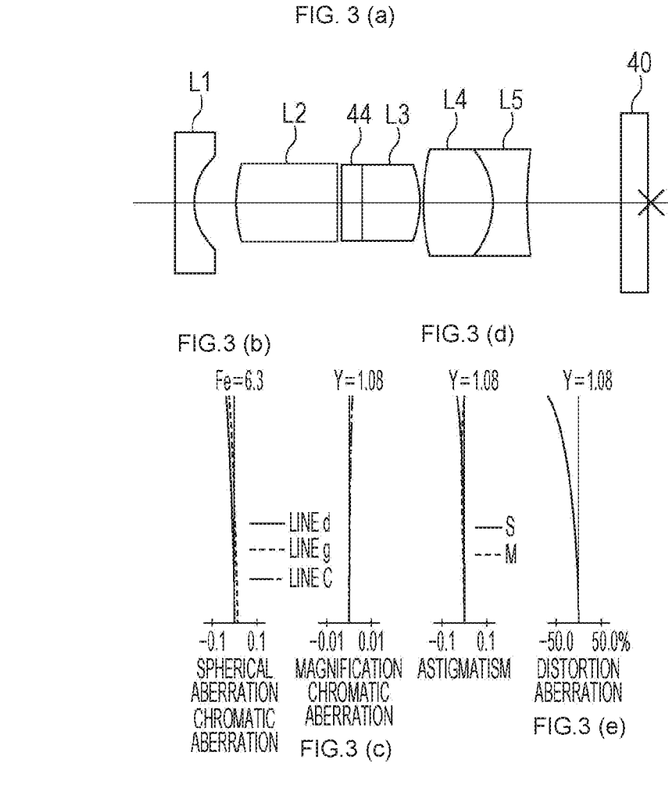
FIGS. 3(a) to 3(e) are diagrams illustrating a lens configuration diagram and various aberration diagrams of a first embodiment.
Figure 4:
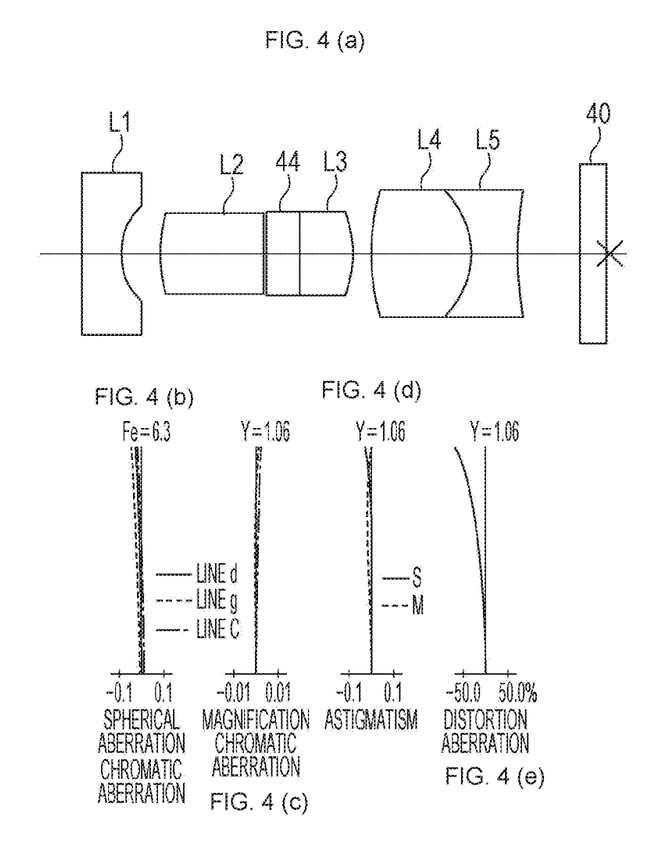
FIGS. 4(a) to 4(e) are diagrams illustrating a lens configuration diagram and various aberration diagrams of a second embodiment.
Figure 5:
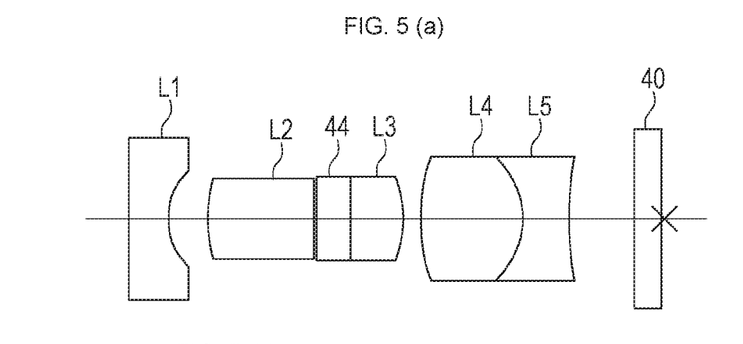
FIGS. 5(a) to 5(e) are diagrams illustrating a lens configuration diagram and various aberration diagrams of a third embodiment.
Figure 6:
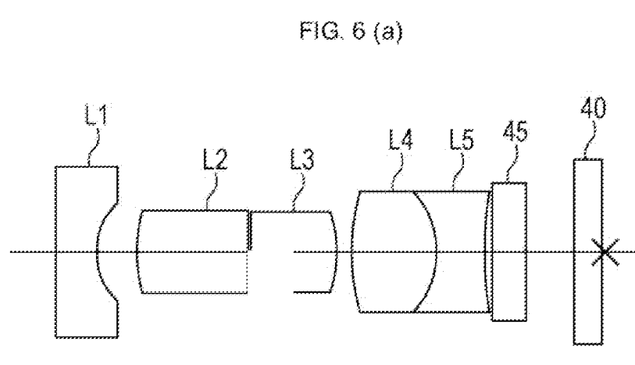
FIGS. 6(a) to 6(e) are diagrams illustrating a lens configuration diagram and various aberration diagrams of a fourth embodiment.

One embodiment of the present invention is an endoscope objective lens unit. Hereinafter, reference numerals of corresponding parts in the embodiment illustrated in FIG. 2 are shown in parentheses as an example. The endoscope objective lens unit includes at least a front lens group having a negative refractive power (front lens group G1), a diaphragm (diaphragm 42), and a rear lens group having a positive refractive power (rear lens group G2), in order from an object side.

The front lens group (front lens group G1) includes at least a negative lens (negative lens L1) having a concave surface on an image side and a positive lens (positive lens L2) having a convex surface on the object side, and the rear lens group (rear lens group G2) includes at least a positive lens (positive lens L3) having, a convex surface facing the image surface side and a cemented lens (cemented lens 46) in which a positive lens and a negative lens are cemented.

In a case where a focal length of the front lens group is $f_F$, a focal length of the rear lens group is $f_R$, and the curvature radiuses of the surface on the object side and the surface on the image surface side of the lens on the image plane side of the cemented lens are respectively $R_{51}$ and $R_{52}$ ($\neq R_{51}$), following expressions (1) and (2) are satisfied.

$$-1.6 < f_F/f_R < -1.2 \qquad (1)$$

$$-1.0 < SF_5 = (R_{51}+R_{52})/(R_{51}-R_{52}) < -0.5 \qquad (2)$$

In a case where an average focal length of the positive lens in the endoscope objective lens unit is $f_P$ and a focal length of the entire system of the endoscope objective lens unit is f, the following expression (3) is preferably satisfied.

$$f_P/f < 2.5 \qquad (3)$$

The image surface side surface of the positive lens (positive lens L2) in the front lens group (front lens group G1) is preferably a plane surface.

In the rear lens group (rear lens group G2), the surface on the object side of the positive lens (positive lens L3) having a convex surface facing the image surface side is preferably a plane surface.

Another aspect of the present invention is an endoscope. The endoscope includes the endoscope objective lens unit, and an image sensor for receiving an object image formed by the endoscope objective lens unit.

Advantageous Effects of Invention

According to the endoscope objective lens unit described above, the configuration of the endoscope objective lens unit that can increase the angle of view while maintaining good optical performance is realized.

DESCRIPTION OF EMBODIMENTS

Figure 1:
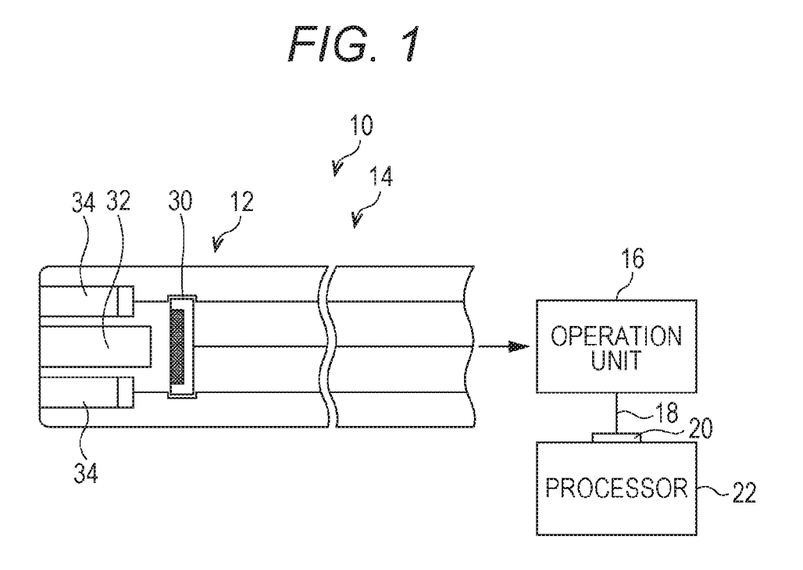
FIG. 1 is a diagram schematically illustrating an example of a configuration of an endoscope equipped with an endoscope objective lens unit according to an embodiment.

Hereinafter, an endoscope objective lens unit and an endoscope according to embodiments will be described with reference to the drawings. FIG. 1 is a diagram schematically illustrating an example of a configuration of an endoscope equipped with the endoscope objective lens unit according to an embodiment.

An endoscope 10 mainly includes a distal end portion 12, a first flexible tube 14, an operation unit 16, a second flexible tube 18, and a connector 20.

The distal end portion 12 includes at least an image sensor 30 that receives and captures an image of a biological tissue, an objective lens unit 32 that forms an image of the biological tissue on the imaging surface of the image sensor 30, and a light source unit 34 arranged near the objective lens unit 32 to illuminate the biological tissue. In addition, the distal end portion 12 may include an ultrasonic diagnostic probe, an opening for discharging fluid such as water or air, or sucking liquid on the biological tissue.

The light source device 34 may be composed of a light source such as a lamp or LED that emits light or may have a configuration including an outlet through which light transmitted from a processor 22 through the optical fiber in the connector 20, the second flexible tube 18, the operation unit 16, and the first flexible tube 14 is emitted.

The image sensor 30 is an image sensor that can acquire incident light having a large incident angle, and is, for example, a CMOS image sensor. The angle of view of the image sensor 30 is larger than 100 degrees, preferably 140 degrees or more.

The first flexible tube 14 is provided with at least a signal line for transmitting an imaging signal of the image sensor 30, a power control line for operating the image sensor 30 and the light source device 34, and various tubes through which a liquid flows.

The operation unit 16 is a part that allows a practitioner to operate the distal end portion 12 so that the distal end portion 12 is placed facing a predetermined position of the biological tissue to observe the biological tissue and treat the biological tissue as necessary.

The second flexible tube 18 is provided with at least a signal line for transmitting a light reception signal of the image sensor 30 and a power control line for operating the image sensor 30 and the light source device 34 therein.

The processor processes imaging signals transmitted via the operation unit 16, the second flexible tube 18, and the connector unit 20, generates an image of the biological tissue, and outputs the image. Further, the processor 22 outputs a control signal for controlling operations of the light source device 34 and the image sensor 30.

An endoscope objective lens unit (hereinafter referred to as an objective lens unit) 32 that forms an image with a wide angle of view suitable for the image sensor 30 with a wide angle of view while maintaining good optical performance is used for such a distal end portion 12. Hereinafter, the objective lens unit 32 will be described. FIG. 2 is a diagram illustrating an example of the configuration of the objective lens unit 32 according to the present embodiment.

The objective lens unit 32 illustrated in FIG. 2 has at least a front lens group G1, a rear lens group G2, and a diaphragm 42. Each lens constituting each lens group G1, G2 has a rotationally symmetric shape with respect to the optical axis AX of the objective lens unit 32. The diaphragm 42 and an optical filter 44 are provided between the front lens group G1 and the rear lens group G2. Further, a cover glass 40 is provided on the light receiving surface (image surface) side of the image sensor 30 from the rear lens group G2. The cover glass 40 is a component provided on the object side of the image sensor 30. In FIG. 2, the focal position of the objective lens unit 32 is indicated by "x" on the image surface side of the cover glass 40.

The optical filter 44 is a near infrared and infrared cut-off filter.

In the objective lens unit 32, the front lens group G1, a diaphragm 42, and the rear lens group G2 including an optical filter 44 are provided in order from the object side to the image surface side; however, the optical filter 44 is not limited to this order.

Note that the objective lens unit 32 having at least the front lens group G1, the rear lens group G2, and the diaphragm 42 may include the optical filter 44 and the cover glass 40 and a configuration in which an optical element having no optical power is added may be included.

Therefore, in one embodiment, the front lens group G1, the rear lens group G2, the cover glass 40, and the diaphragm 42 are provided. In another embodiment, a front lens group G1, a rear lens group G2, a cover glass 40, a diaphragm 42, and an optical filter 44 are provided. In another embodiment, a front lens group G1, a rear lens group G2, a diaphragm 42, and an optical filter 44 are provided.

The front lens group G1 is a lens group having negative refractive power on the object side with respect to the diaphragm 42.

The front lens group G1 includes at least a negative lens L1 having a concave surface facing the image surface side and a positive lens L2 having a convex surface facing the object side. The description that the front lens group G1 includes at least the negative lens L1 and the positive lens L2 means that other lenses having substantially no optical power may be included.

The rear lens group G2 is a lens group having a positive refractive power on the image surface side with respect to the diaphragm 42. The rear lens group G2 includes at least a positive lens L3 having a convex surface facing the image surface side, and a cemented lens 46 in which a positive lens L4 and a negative lens L5 are cemented. The description that the rear lens group G2 includes at least the positive lens L3 and the cemented lens 46 means that other lenses having substantially no optical power may be included.

According to one embodiment, as illustrated in FIG. 2, the negative lens L1 has a plane surface on the object side, the positive lens L2 has a plane surface on the image surface side, the positive lens L3 has a plane surface on the object side, the positive lens L4 has a convex surface on the image surface side and a convex surface on the object side, and the negative lens L5 has a concave surface on the image surface side and a concave surface on the object side.

In the objective lens unit 32 including the front lens group G1 and the rear lens group G2 having such a configuration, in a case where the focal length of the front lens group G1 is $f_F$, the focal length of the rear lens group G2 is set to fry, and curvature radiuses of die surface 46a on the object side and the surface 46b on the image surface of the negative lens L5, which is on the image surface side, of the cemented lens 46 are respectively $R_{51}$ and $R_{52}$ ($\neq R_{51}$, that is, $R_{52}$ is different from $R_{51}$), the following expressions (1) and (2) are satisfied.

$$-1.6 < f_F/f_R < -1.2 \qquad \text{Expression (1)}$$

$$-1.0 < SF_5 = (R_{51}+R_{52})/(R_{51}-R_{52}) < -0.5 \qquad \text{Expression (2)}$$

The objective lens unit 32 that satisfies the expressions (1) and (2) can shorten the exit pupil distance and increase the angle of view while maintaining good optical performance. For example, the angle of view can be made larger than 100 degrees, preferably 120 degrees or more, more preferably 140 degrees or more, and further preferably 140 degrees or more and 170 degrees or less. In general, when the viewing angle of the objective lens unit 32 is widened, the outer diameter of the objective lens unit 32 is increased, and the overall length of the objective lens unit 32 is shortened; however, it is not preferable that outer diameter of the objective lens unit 32 is increased at the narrow distal end portion 12. The objective lens unit 32 that satisfies the expressions (1) and (2) can maintain a long and narrow shape and widen the viewing angle.

When $f_F/f_R$ is set to −1.6 or less, the negative refractive power of the front lens group G1 (hereinafter, the refractive power is referred to as power) becomes weak, and the viewing angle becomes narrower. To widen the viewing angle, the outer diameter of the front lens group G1 may be increased; however, this makes difficult to form the objective lens unit 32 elongated.

On the other hand, when $f_F/f_R$ is set to −1.2 or more, the positive power of the rear lens group G2 becomes weak, so the overall length of the objective lens unit 32 becomes long, and this is not preferable when the image sensor 30 and the objective lens unit 32 are arranged at the small distal end portion 12.

From the above point of view, $f_F/f_R$ is less than −1.2, preferably −1.25 or less, more preferably −1.3 or less, and particularly preferably −1.35 or less. Further, $f_F/f_R$ is larger than −1.6, preferably −1.55 or more, and more preferably −1.51 or more.

On the other hand, $SF_5 = (R_{51}+R_{52})/(R_{51}-R_{52})$ in Expression (2) is a shape factor that defines the shape of the surface of the lens L5, which affects the light emission angle to the light receiving surface of the image sensor 30 and the exit pupil distance, and affects the chromatic aberration.

Outside the upper limit of the range defined in Expression (2), the light emission angle at the cemented lens 46 increases, and the off-axis F number increases, so the periphery becomes dark.

Further, outside the lower limit of the range defined in Expression (2), the exit pupil distance becomes longer and the field angle becomes smaller. In addition, there is a problem that the curvature radius of the cemented surface of the cemented lens 46 becomes small, and it is difficult to correct chromatic aberration.

From the above point of view, $SF_5$ is larger than −1.0 and smaller than −0.5, but $SF_5$ is preferably −0.8 or more, and more preferably −0.75 or more. Furthermore, $SF_5$ is preferably −0.55 or less, and more preferably −0.6 or less.

Moreover, it is preferable that, in a case where the average value (simple average value) of the focal lengths of the positive lenses in the objective lens unit 32 is $f_P$ and the focal length of the entire system of the objective lens unit 32 is f, the following expression (3) is satisfied.

$$f_P/f < 2.5 \qquad \text{Expression (3):}$$

When $f_P/f$ is 2.5 or more, the power of the positive lens in the objective lens unit 32 becomes small, and the magnification greatly changes. For this reason, the change in the focal length of the entire system of the objective lens unit 32 caused by the thickness of the positive lens or the change in the distance between the lenses in the front and rear of the optical axis AX direction of the diaphragm 42 becomes large, and this may often cause a large change in the viewing angle. From such a point of view, $f_P/f$ is preferably less than 2.5, more preferably 2.0 or less, and even more preferably 1.9 or less.

Although there is no restriction in the minimum of $f_P/f$, $f_P/f$ is 1.65 or more according to one embodiment, and 1.7 or more according to one embodiment.

According to one embodiment, the surface on the image surface side of the positive lens L2 is a plane surface. Further, according to one embodiment, the front lens group G1 includes the negative lens L1 having the concave surface facing the image surface side and the positive lens L2 having the plane surface facing the image surface side, in order from the object side. In this manner, by making the surface on the image surface side of the positive lens L2 a plane surface, a change in magnification and a change in angle of view due to a change in the lens thickness can be suppressed.

According to one embodiment, the surface on the object side surface of the positive lens L3 is a plane surface. Further, according to one embodiment, the lenses of the rear lens group G2 are configured by the positive lens L3 having a plane surface facing the object side and the cemented lens 46, in order from the object side. At this time, the surface on the object side of the positive lens L3 is a plane surface. In this manner, by making the surface on the object side of the positive lens L3 a plane surface, a change in magnification and a change in the angle of view caused by a change in the lens thickness can be suppressed. In addition, since the cemented lens 46 including the positive lens L4 having the convex surface facing the object side and the negative lens L5 having the concave surface facing the image surface side and the concave surface facing the object side is provided, it is possible to suppress chromatic aberration while suppressing a change in the emission angle.

According to one embodiment, as illustrated in FIG. 2, in the front lens group G1, the lenses L1 and L2 are preferably arranged so that the concave surface on the image surface side of the negative lens L1 and the convex surface on the object side of the positive lens L2 are adjacent to each other and face each other and, in the rear lens group G2, the lens L3 and the cemented lens 46 are preferably arranged so that the convex surface on the image side of the positive lens L3 and the convex surface on the object side of the positive lens L4 of the cemented lens 46 adjacent to each other and face each other.

First to Fourth Embodiments

Specific numerical examples of the objective lens unit 32 configured as described above are described in Tables 1 to 4 below (the first to fourth embodiments). The half angle of view in the first to fourth embodiments is 72 degrees or more.

Figure 7:
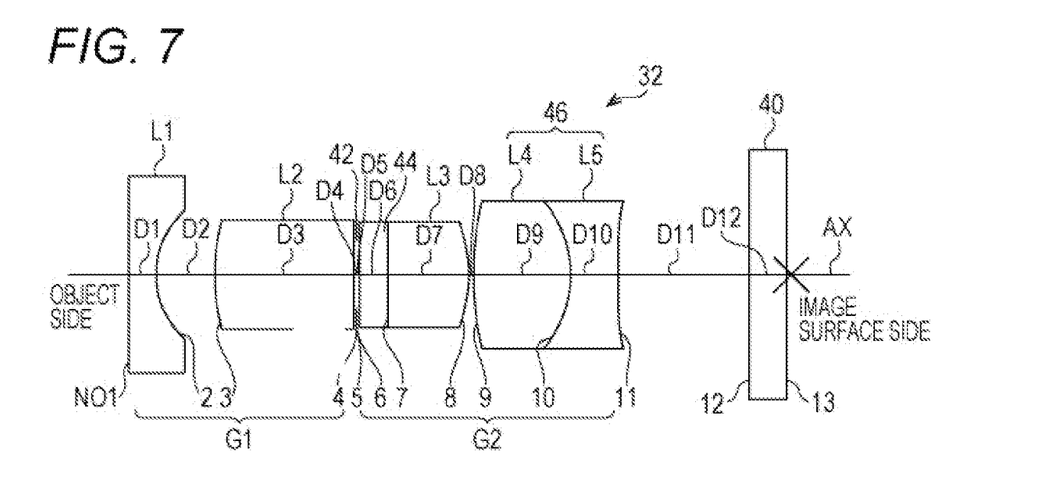
FIG. 7 is a diagram illustrating a configuration in specifications of the first to third embodiments.
Figure 8:
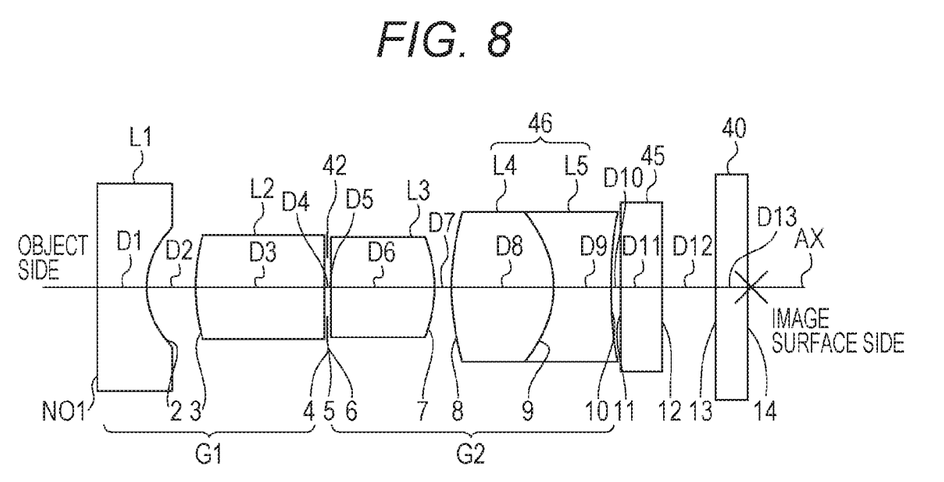
FIG. 8 is a diagram illustrating a configuration according to specifications of the fourth embodiment.

On the other hand, lens configuration diagrams and various aberration diagrams of the objective lens unit 32 are illustrated in FIGS. 3 to 6. In FIGS. 3 to 6(a), the diaphragm 42 is not illustrated. FIGS. 3 to 6(b)-(e) illustrate various aberration diagrams of the first to fourth embodiments. The configurations of the first to third embodiments are as illustrated in FIG. 2. FIG. 7 is a diagram illustrating configuration information in the specifications of the first to third embodiments. The configuration of the fourth embodiment is as illustrated in FIG. 8. FIG. 8 is a diagram illustrating configuration information in the specification of the fourth embodiment.

Among the aberration diagrams in FIGS. 3 to 6(b)-(e), (b) illustrates spherical aberration and axial chromatic aberration at the line d (588 nm), line g (436 nm), and line C (656 nm). (c) illustrates magnification chromatic aberration at the line d, line g, and line C. In (b) and (c), the solid line indicates the aberration at the line d, the dotted line indicates the aberration at the line g, and the alternate long and short dash line indicates the aberration at the line C. (d) illustrates astigmatism. In (d), the solid line indicates the sagittal component (5), and the dotted line indicates the meridional component (M). (e) illustrates distortion aberration. Fe indicated in the aberration diagrams represents an effective F number. Y represents an image height.

FIGS. 3 to 6(b)-(d), the vertical axis represents the image height (mm), and the horizontal axis represents the aberration amount (mm). FIGS. 3 to 6(e), the vertical axis represents the image height (mm), and the horizontal axis represents the distortion rate.

The specifications of the first embodiment are as described in Table 1 below. The configuration in the specifications of the first to third embodiments is as illustrated in FIG. 7. FIGS. 3(b) to 3(e) illustrate various aberration diagrams of the first embodiment. In Table 1, NO represents the surface of the optical element such as the lens, diaphragm, optical filter, cover glass, etc. illustrated in FIG. 7, R represents the curvature radius (mm) of the surface, and D represents the distance (mm) along the optical axis AX from each surface to the surface adjacent to the image surface side. In the curvature radius R, a positive value represents a surface convex toward the object side, and a negative value represents a surface convex toward the image surface side. In Table 1, the distances D of NO1 to NO12 are the distances of D1 to D12 defined in FIG. 7. N(d) represents the refractive index at the line d, and μd represents its Abbe number. f in Table 1 represents a focal length (mm) in the entire system of the objective lens unit 32. The first embodiment described in Table 1 includes seven lenses, optical filters, and cover glasses. In Tables 2 and 3, each specification is described in the same format as Table 1. In Tables 1 to 3, Rs of NO10 and 11 correspond to $R_{S1}$ and $R_{S2}$, that define SF, respectively.

TABLE 1

| NO | R | D | N(d) | νd |
|---|---|---|---|---|
| 1 | INFINITY | 0.240 | 1.88300 | 40.8 |
| 2 | 0.765 | 0.490 | | |
| 3 | 1.786 | 1.200 | 1.77250 | 49.6 |
| 4 | INFINITY | 0.000 | | |
| 5 Diaphragm | INFINITY | 0.024 | | |
| 6 | INFINITY | 0.240 | 1.52249 | 59.8 |
| 7 | INFINITY | 0.682 | 1.77250 | 49.6 |
| 8 | −1.324 | 0.040 | | |
| 9 | 2.734 | 0.823 | 1.72916 | 54.7 |
| 10 | −1.012 | 0.400 | 1.84666 | 23.8 |
| 11 | 5.849 | 1.109 | | |
| 12 | INFINITY | 0.320 | 1.52249 | 59.8 |
| 13 | INFINITY | — | | |

| Effective F number Fe | 6.3 |
| Focal length f | 1.00 |
| Magnification | −0.121 |
| Half angle of view (degrees) | 74 |
| Image height (mm) | 1.08 |

The specifications of the second embodiment are as described in Table 2 below. FIGS. 4(b) to (e) illustrate various aberration diagrams of the second embodiment.

TABLE 2

| NO | R | D | N(d) | νd |
|---|---|---|---|---|
| 1 | INFINITY | 0.470 | 1.88300 | 40.8 |
| 2 | 0.783 | 0.456 | | |
| 3 | 1.907 | 1.221 | 1.77250 | 49.6 |
| 4 | INFINITY | 0.000 | | |
| 5 Diaphragm | INFINITY | 0.024 | | |
| 6 | INFINITY | 0.392 | 1.54200 | 63.8 |
| 7 | INFINITY | 0.622 | 1.77250 | 49.6 |
| 8 | −1.450 | 0.217 | | |
| 9 | 2.378 | 1.176 | 1.72916 | 54.7 |
| 10 | −1.064 | 0.549 | 1.84666 | 23.8 |
| 11 | 4.661 | 0.722 | | |
| 12 | INFINITY | 0.314 | 1.52249 | 59.8 |
| 13 | INFINITY | — | | |

| Effective F number Fe | 6.3 |
| Focal length f | 1.00 |
| Magnification | −0.122 |
| Half angle of view (degrees) | 72.5 |
| Image height (mm) | 1.06 |

The specifications of the third embodiment are as described in Table 3 below. FIGS. 5(b) to (e) illustrate various aberration diagrams of the third embodiment

TABLE 3

| NO | R | D | N(d) | νd |
|---|---|---|---|---|
| 1 | INFINITY | 0.472 | 1.88300 | 40.8 |
| 2 | 0.775 | 0.464 | | |
| 3 | 2.009 | 1.259 | 1.77250 | 49.6 |
| 4 | INFINITY | 0.000 | | |
| 5 Diaphragm | INFINITY | 0.024 | | |
| 6 | INFINITY | 0.394 | 1.54200 | 63.8 |
| 7 | INFINITY | 0.614 | 1.77250 | 49.6 |
| 8 | −1.434 | 0.212 | | |
| 9 | 2.444 | 1.181 | 1.72916 | 54.7 |
| 10 | −1.093 | 0.551 | 1.84666 | 23.8 |
| 11 | 4.436 | 0.767 | | |
| 12 | INFINITY | 0.315 | 1.52249 | 59.8 |
| 13 | INFINITY | — | | |

| Effective F number Fe | 6.3 |
| Focal length f | 1.00 |
| Magnification | −0.121 |
| Half angle of view (degrees) | 73.1 |
| Image height (mm) | 1.07 |

The specifications of the fourth embodiment are as described in Table 4 below. FIG. 6(a) illustrates a configuration, and FIGS. 6(b) to 6(e) illustrate various aberration diagrams of the fourth embodiment. In Table 4, NO represents the surface of the optical element such as the lens, diaphragm, optical filter, cover glass, etc. illustrated in FIG. 8, R represents the curvature radius (mm) of the surface, and D represents the distance (mm) along the optical axis AX from each surface to the surface adjacent to the image surface side. In the curvature radius R, a positive value represents a surface convex toward the object side, and a negative value represents a surface convex toward the image surface side. In Table 4, the distances D of NO1 to NO13 are the distances of D1 to D13 defined in FIG. 8. N(d) represents the refractive index at the line d, and μd represents its Abbe number. In the fourth embodiment illustrated in Table 4, seven optical elements are provided. f represents the focal length (mm) in the entire system of the objective lens unit 32. In the fourth embodiment, as illustrated in FIG. 8, an optical filter 45 is disposed between the negative lens L5 and the cover glass 40 in place of the optical filter 44 illustrated in FIG. 7. In Table 4, Rs of NO9 and 10 correspond to $R_{51}$ and $R_{52}$ that define SF, respectively,

TABLE 4

| NO | R | D | N(d) | vd |
|---|---|---|---|---|
| 1 | INFINITY | 0.472 | 1.88300 | 40.8 |
| 2 | 0.784 | 0.456 | | |
| 3 | 2.014 | 1.258 | 1.77250 | 49.6 |
| 4 | INFINITY | 0.000 | | |
| 5 Diaphragm | INFINITY | 0.024 | | |
| 6 | INFINITY | 0.998 | 1.77250 | 49.6 |
| 7 | −1.370 | 0.157 | | |
| 8 | 2.425 | 0.975 | 1.72916 | 54.7 |
| 9 | −1.045 | 0.550 | 1.84666 | 23.8 |
| 10 | 4.480 | 0.079 | | |
| 11 | INFINITY | 0.393 | 1.54200 | 63.8 |
| 12 | INFINITY | 0.549 | | |
| 13 | INFINITY | 0.314 | 1.52249 | 59.8 |
| 14 | INFINITY | — | | |

| | |
|---|---|
| Effective F number Fe | 6.2 |
| Focal length f | 1.00 |
| Magnification | −0.121 |
| Half angle of view (degrees) | 72.2 |
| Image height (mm) | 1.07 |

As can be seen from the aberration diagrams illustrated in FIGS. 3 to 6(b)-(e), all the aberrations of the first to fourth embodiments are preferably corrected.

The focal length ratios and $SF_5$ of the first to fourth embodiments are shown in Table 5 below

TABLE 5

| | First embodiment | Second embodiment | Third embodiment | Fourth embodiment |
|---|---|---|---|---|
| $f_F/f_R$ | −1.51 | −1.45 | −1.35 | −1.38 |
| $SF_5$ | −0.71 | −0.63 | −0.61 | −0.62 |
| $f_P/f$ | 1.71 | 1.84 | 1.89 | 1.82 |

As described in Table 5, the first to fourth embodiments satisfy the above expressions (1) and (2).

From this, the objective lens unit that satisfies the above expressions (1) and (2) can shorten the exit pupil distance, can make the angle of view larger than 100 degrees, and can be made 140 degrees or more, and thus, the aberration characteristics can be kept preferable. Therefore, this embodiment can provide an objective lens unit for an endoscope that compatible with an image sensor with a wide angle of view.

The endoscope objective lens unit and the endoscope according to the present embodiment have been described above; however, the present invention is not limited to the above described configuration, and various modifications can be made within the scope of the technical idea of the present invention.

REFERENCE SIGNS LIST

10 Endoscope
12 Distal end portion
14 First flexible tube
16 Operation unit
18 Second flexible tube
20 Connector
22 Processor
30 Image sensor
32 Objective lens unit
34 Light source unit
40 Cover glass
42 Diaphragm
44, 45 Optical filter
46 Cemented lens

The invention claimed is:

1. An endoscope objective lens unit comprising:
at least a front lens group having a negative refractive power, a diaphragm, and a rear lens group having a positive refractive power in order from an object side, wherein
the front lens group includes at least a negative lens having a concave surface facing an image surface side and a positive lens having a convex surface facing the object side,
the rear lens group includes at least a positive lens having a convex surface facing the image surface side and a cemented lens in which the positive lens and a negative lens are cemented,
the negative lens of the cemented lens is on the image surface side of the cemented lens, and
in a case where a focal length of the front lens group is $f_F$, a focal length of the rear lens group is $f_R$, curvature radiuses of a surface on the object side of the negative lens of the cemented lens is $R_{51}$, and a surface on the image surface side of the negative lens of the cemented lens is $R_{52}$ ($\neq R_{51}$), the following expressions (1) and (2) are satisfied:

$$-1.6 < f_F/f_R < -1.2; \text{ and} \quad (1)$$

$$-1.0 < SF_5 = (R_{51}+R_{52})/(R_{51}-R_{52}) < -0.5. \quad (2)$$

2. The endoscope objective lens unit according to claim 1, wherein, in a case where an average focal length of positive lenses in the endoscope objective lens unit is $f_P$ and a focal length of the entire system of the endoscope objective lens unit is f, a following expression (3) is satisfied:

$$f_P/f < 2.5. \quad (3)$$

3. The endoscope objective lens unit according to claim 1, wherein a surface on an image surface side of the positive lens, in the front lens group, is a plane surface.

4. The endoscope objective lens unit according to claim 1, wherein a surface on an object side of the positive lens having a convex surface facing the image surface side, in the rear lens group, is a plane surface.

5. An endoscope comprising:
the endoscope objective lens unit according to claim 1; and
an image sensor that receives an object image formed by the endoscope objective lens unit.

* * * * *